Aug. 13, 1974 G. MERRILL Plant Pat. 3,590
PEACH PLANT
Filed Oct. 3, 1972
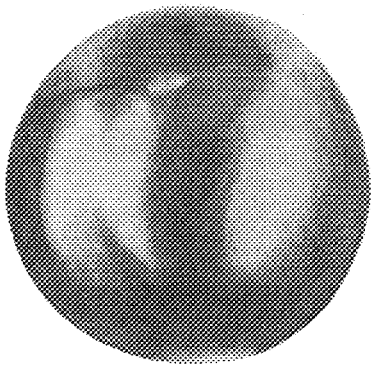
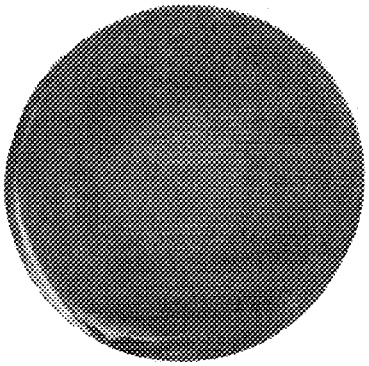

United States Patent Office

Plant Pat. 3,590
Patented Aug. 13, 1974

3,590
PEACH PLANT

Grant Merrill, 416 N. Anderson Road,
Exeter, Calif. 93221

Filed Oct. 3, 1972, Ser. No. 294,670
Int. Cl. A01h *5/03*
U.S. Cl. Plt.—43 1 Claim

ABSTRACT OF THE DISCLOSURE

The present invention relates to a peach tree and more particularly to a new and distinct variety thereof broadly characterized by a tree of medium size which bears freestone fruit with from half to almost all of its skin surface covered with brilliant red, and when ripe has yellow flesh that is firm on the outside, allowing for easy commercial handling, but riper on the inside, thus permitting all of the fruit to be picked at one time, or when properly pruned to be harvested mechanically in one picking.

The instant variety of peach most nearly resembles Red Lady, also known as Scarlet Lady 2 (Plant Pat. 2,601), but is an improvement thereon in being a more vigorous tree and bearing fruit that ripens about one week later.

I originated the present variety of peach on a farm formerly owned by me near Red Bluff, Tehama County, Calif., by planting seeds from open pollinated blossoms of Red Lady and after the resulting tree came into bearing, moving it to Tulare County, Calif., where the tree was grafted into test orchards in Tulare and Fresno Counties, asexually reproducing the instant variety. The instant variety proved to have the same fruit and tree characteristics as the original tree and to be worthy of commercial use.

The accompanying drawing is an oil painting of a characteristic mature fruit of the subject variety showing the shape and skin color.

Referring now more specifically to the promological characteristics of this new and distinct variety of peach tree, the following is an outline description thereof observed under the ecological conditions prevailing in Tulare County, Calif. All major color plate identifications are by reference to Maerz and Paul's Dictionary of Color, First Edition.

TREE

Size: Medium to large, may be pruned to vase shape.
Trunk: Straight, medium stocky, gray and shaggy on mature trees, brown on young trees.
Branches: Medium stocky, gray and shaggy on mature trees, brown on young trees.
Lenticels: Medium size and quantity.
Twigs: Medium length, red-brown when mature, green when young.

LEAVES

Source: Selected from mid-portion of terminal shoots 12 to 24 inches long.
Shape: Lanceloate, tip acuminate.
Size: Generally medium in size, main leaves 5 to 7½ inches long, ⅞ to 1¾ inches wide, medium thin.
Color: Dark green on upper surface, light green on lower surface, viens very light yellow-green.
Class: Classes 2 and 3 on main leaves. Meader and Blake: Proceedings of the American Society for Horticultural Science, Vol. 36.
Margin: Crenate.
Petiole: Medium size, about ½ inch long.
Glands: Reniform, usually about three.
Stipules: At base of leaf, dropping off early.

FLOWERS

Buds: Medium size, pubescent, plump, free.
Blossoms: Small to medium in size, pink, to pinkish salmon.
Pollen: Abundant.

FRUIT

Season: Described at maturity. Firm ripe first week of July.
Size: Medium to large, 2½ to 3⅛ inch axially, 2⅝ to 2⅞ inch transverse in suture plane, 2⅝ to 2⅞ inch at right angle to suture plane.
Form: Variable. Generally cordate, some globose with slight tip.
Suture: Inconspicuous to shallow, extends from base beyond but discontinuous at apex, slight depression beyoung pistil point. Dorsal surface rounded.
Cavity: Flaring, somewhat abruptly, elongated in suture plane, some almost round; ½ to 11/16 inch to depth, ½ to ¾ inch in breadth, apex mucronate, pistil point apical.
Stem: Medium size, generally about ⅜ inch long, ⅛ inch in diameter.
Skin: Medium thin, sweet, tenacious to flesh unless very ripe; short, scant pubescense; color light red blush 5K10 and 5K11 to dark red blush 5L11 over an undercolor of light yellow 9L3 to medium yellow 9L6 and 9L7, to orange yellow 11L10, as illustrated with one fruit showing yellow side and the other fruit showing nearly all red on the skin surface.
Flesh: Yellow, strongly red around stone, moderate amygdalin, generally firm texture softening first next to stone, retaining firmness at surface until nearly over ripe; distinct aroma; good eating quality.

STONE

Tenacity: Completely free.
Fibers: Short, few.
Size: Medium, 1¾ to 1⅞ inches in length, ¾ to 1 inch in width.
Form: Generally obovate with acuminate tip and generally oblique base; oval hilum, acuminate apex, generally equal sides but few unequal.
Surface: Irregularly furrowed and pitted surface.
Ventral edge: Thick, with thin grooves.
Dorsal edge: Deep furrows on either side interrupted toward apex.
Color: Reddish brown when fresh, tan when dried.
Tendency to split: Slight.

USE

Markets: Nearby and long distance.
Quality: Good eating.

Although the new variety of peach possesses the described characteristics under the growing conditions near Exeter, Tulare County, Calif., having first been observed near Red Bluff, Tehama County, Calif., it is to be understood that variations of the usual magnitude in the characteristics incident to the growing conditions, fertilization, pruning, thinning and pest control are to be expected.

Having thus described and illustrated the distinct qualities of my new variety of peach tree, what is claimed is:

1. A new and distinct variety of peach tree substantially as illustrated and described and particularly characterized as being a medium size tree regularly bearing large fruit having a surface covering of brilliant red over from half to almost all of its surface and with freestone yellow flesh that stays firm near the surface when ripe so it may be picked in one picking, or when properly pruned may be mechanically harvested in one picking, and which most nearly resembles Red Lady, also known as Scarlet Lady 2 (Plant Pat. 2,601), but is an improvement thereon in that it is a more vigorous tree and ripens its fruit about a week later.

No references cited.

ROBERT E. BAGWILL, Primary Examiner